US008075873B2

(12) United States Patent
Zeng

(10) Patent No.: US 8,075,873 B2
(45) Date of Patent: Dec. 13, 2011

(54) METHOD OF PREPARING DRY POWDER INHALATION COMPOSITIONS

(75) Inventor: Xian-Ming Zeng, Surrey (GB)

(73) Assignee: Norton Healthcare Limited, London (GB)

( * ) Notice: Subject to any disclaimer, the term of this patent is extended or adjusted under 35 U.S.C. 154(b) by 144 days.

(21) Appl. No.: 12/387,760

(22) Filed: May 6, 2009

(65) Prior Publication Data

US 2009/0264389 A1   Oct. 22, 2009

Related U.S. Application Data

(63) Continuation of application No. 10/646,363, filed on Aug. 21, 2003, now abandoned.

(30) Foreign Application Priority Data

Aug. 21, 2002 (GB) .................................. 0219511.3

(51) Int. Cl.
*A61K 9/14* (2006.01)
*A61K 9/00* (2006.01)
(52) U.S. Cl. ......................................... 424/46; 424/489
(58) Field of Classification Search ................... 424/46, 424/489
See application file for complete search history.

(56) References Cited

U.S. PATENT DOCUMENTS

| | | | |
|---|---|---|---|
| 3,957,965 A | 5/1976 | Hartley et al. |
| 3,994,974 A | 11/1976 | Murakami et al. |
| 4,937,254 A | 6/1990 | Sheffield et al. |
| 5,684,199 A | 11/1997 | Francotte et al. |
| 5,972,919 A | 10/1999 | Carling et al. |
| 5,985,248 A | 11/1999 | Gordon et al. |
| 6,017,963 A | 1/2000 | Alfonso et al. |
| 6,030,604 A | 2/2000 | Trofast |
| 6,071,971 A | 6/2000 | Senanayake |
| 6,103,270 A | 8/2000 | Johnson et al. |
| 6,199,607 B1 | 3/2001 | Trofast et al. |
| 6,284,287 B1 | 9/2001 | Sarlikiotis et al. |
| 6,616,914 B2 | 9/2003 | Ward et al. |
| 6,645,466 B1 | 11/2003 | Keller et al. |
| 6,737,044 B1 | 5/2004 | Dickinson et al. |
| RE38,912 E | 12/2005 | Walz et al. |
| 7,090,870 B1 | 8/2006 | Vanderbist et al. |
| 2002/0018753 A1 | 2/2002 | Blondino et al. |
| 2002/0081266 A1 | 6/2002 | Woolfe et al. |
| 2002/0103260 A1 | 8/2002 | Clarke et al. |
| 2002/0106332 A1 | 8/2002 | Walz et al. |
| 2002/0110529 A1 | 8/2002 | Karoline et al. |
| 2003/0118514 A1 | 6/2003 | Larhrib et al. |
| 2003/0133880 A1 | 7/2003 | Musa et al. |
| 2004/0258626 A1 | 12/2004 | Zeng |
| 2005/0158248 A1 | 7/2005 | Zeng |
| 2006/0029552 A1 | 2/2006 | Staniforth |
| 2006/0292083 A1 | 12/2006 | Zeng |
| 2007/0189979 A1 | 8/2007 | Zeng et al. |
| 2008/0131518 A1 | 6/2008 | Zeng et al. |

FOREIGN PATENT DOCUMENTS

| | | |
|---|---|---|
| WO | 01/39745 | 6/1992 |
| WO | 98/31352 | 7/1998 |
| WO | 98/31353 | 7/1998 |
| WO | 9850015 A1 | 11/1998 |
| WO | 99/51205 A1 | 10/1999 |
| WO | WO 99/64014 | 12/1999 |
| WO | 00/28979 | 5/2000 |
| WO | WO 00/53158 | 9/2000 |
| WO | 92/10229 | 6/2001 |
| WO | WO 01/70198 A1 | 9/2001 |
| WO | WO 01/78737 A1 | 10/2001 |
| WO | WO 01/89491 | 11/2001 |
| WO | WO 01/89492 A1 | 11/2001 |

OTHER PUBLICATIONS

W. Carius, Process Monitoring with High-Shear High Intensity Mixers/Power Consumption Measurement in Pilot Plant Laboratory, Pharmazeutische Industrie, (1992) vol. 54, No. 6, pp. 543-546.
DMV-Fonterra Excipients: "Pharmatose, milled and sieved lactose". [online] XP002529164 URL:www.dmv-fontera-excipients.com. Retrieved May 25, 2009.
Xian Ming Zeng et al., The influence of Lactose Carrier on the Content Homogeneity and Dispersibility of Beclomethansone Dipropionate from Dry Powder Aerosols, Int'l Journal of Pharmaceutics, Elsevier BV, NL, (2000), vol. 107. No. 1/02, pp. 41-52.
Goodman and Gilman's The PharmacoIogical Basis of Therapeutics, 10th Ed., McGraw Hill Companies Inc., Newyork 2001, pp. 1701-1704.
Gennaro, "Pharmaceutical Necessities", Remington's Pharmaceutical Sciences 18th Ed., MACK Publishing Co., Easton PA1990, pp. 1286-1329.
Gennaro, "Oral Solid Dosage Forms", Remington's Pharmaceutical Sciences 18th Ed., MACK Publishing Co., Easton PA1990, pp. 1635-1638.
O'Connor et al, "Powders", Remington: The Science and Practice of Pharmacy, 19th Ed., Lippincott, Williams & Wilkinsi 1995, pp. 1598-1614.
Zeng et al, "Carrier Particles", Particulate Interactions in Dry Podwer Formulations fcr Inhalation, Taylor & Francis 2001 pp. 144-151.
Office Action and Response from U.S. Appl. No. 10/646,362, dated Jun. 29, 2007 and Mar. 29, 2007, respectively.
Office Action and Response from U.S. Appl. No. 10/646,361, dated Jun. 25, 2007 and Jan. 29, 2009, respectively.
Merriam-Webster's Collegiate Dictionary, 10th edition, Merriam-Webster Incorporated: Springfield Massachusetts, 1993, pp. 311.
Vippaaunta et al. "Crystalline Solids," Advanced Drug Delivery Reviews, 2001, 48, pp. 18.

*Primary Examiner* — James H. Alstrum-Acevedo
(74) *Attorney, Agent, or Firm* — RatnerPrestia

(57) ABSTRACT

The invention provides a method of preparing a dry powder inhalation composition comprising a pharmaceutically acceptable particulate carrier, a first particulate inhalant medicament and a second particulate inhalant medicament. Also provided are dry powder compositions and methods of using them with a dry powder inhalation device.

23 Claims, No Drawings

METHOD OF PREPARING DRY POWDER INHALATION COMPOSITIONS

CROSS-REFERENCE TO RELATED APPLICATIONS

This application is a continuation of U.S. application Ser. No. 10/646,363, filed on Aug. 21, 2003, which claims the benefit of the filing date of United Kingdom Patent Application No. 0219511.3, filed Aug. 21, 2002, all of which are incorporated herein by reference.

TECHNICAL FIELD OF THE INVENTION

The invention relates to methods of preparing dry powder inhalation compositions, compositions and uses of the same. The compositions of the invention are characterized by dose uniformity, reliability and dispersion of medicaments uniformity.

BACKGROUND OF THE INVENTION

The preparation of ternary mixtures of a particulate carrier, a first particulate inhalant medicament and a second particulate inhalant medicament poses particular problems when one medicament is present at a relatively small proportion compared to the other medicament. It is difficult to prepare mixtures which are homogeneous. In addition, small quantities of medicament may sometimes bind to the inert carrier, which can affect the amount of medicament that is made available to the patient when the formulation is delivered, e.g. by means of a dry powder inhaler (DPI) device. In such devices, a metered dose of composition comprising one or more active ingredients and an inert carrier, such as lactose, is dispensed into the air stream that is produced by the inspirational effort of the patient. The medicaments and carrier are entrained in this air stream, with only the fine particles of medicament entering the deep recesses of the lung (which is the site of action of the medicament), the inert excipient being deposited either in the mouth or in the upper region of the lungs.

The accurate metering of highly potent inhalant drugs causes particular problems, as the quantity of medicament in the composition relative to that of the carrier is often particularly small (less than 1 part of drug to 50 parts of carrier). This is exemplified by the medicament formoterol, which is often administered to patients at a dose of less than 60 micrograms (doses may be as small as 6 micrograms).

Thus, methods of producing ternary mixtures that are homogeneous and can be used with suitable dry powder inhalers, to give dose uniformity, reliability, and uniform dispersion of a plurality of medicaments in the composition are needed.

SUMMARY OF THE INVENTION

It has been discovered that dry powder preparations characterised by dose uniformity, reliability and dispersion of medicaments uniformity may be obtained by mixing specified ratios of medicaments to carrier in a specified manner as described herein. Thus, the invention provides a method of preparing a dry powder inhalation composition comprising a pharmaceutically acceptable particulate carrier, a first particulate inhalant medicament and a second particulate inhalant medicament, where the proportion of the second medicament to the carrier is smaller relative to the proportion of the first medicament to the carrier. The method is characterised in that the carrier is mixed with a first portion of the first particulate inhalant medicament, the resulting first mixture is mixed with substantially all of the second particulate inhalant medicament to give a mixture. The remaining portion of the first particulate inhalant medicament is mixed with the second mixture to give the desired dry powder inhalation composition. Also provided are dry powder inhalation compositions and methods of using them with a dry powder inhalation device. The invention additionally provides a method for the administration of a therapeutically effective amount of the compositions of the invention for the treatment of conditions responsive to the medicament(s) of choice.

DETAILED DESCRIPTION OF THE INVENTION

The invention provides a method of preparing a dry powder inhalation composition comprising a carrier, and first and second particulate medicament. The method is characterised in that the carrier is mixed with a first portion of the first medicament, the resulting mixture is mixed with substantially all of the second medicament to give a pre-mixture and then the remaining portion of the first medicament is mixed with the pre-mixture to give the desired dry powder inhalation composition. Also provided are dry powder compositions and methods of using them with a dry powder inhalation device.

The patents, published applications, and scientific literature referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's The Pharmacological Basis of Therapeutics, 10.sup.th Ed., McGraw Hill Companies Inc., New York (2001).

Any suitable materials and/or methods known to those of skill can be utilized in carrying out the present invention. However, preferred materials and methods are described. Materials, reagents and the like to which reference is made in the following description and examples are obtainable from commercial sources, unless otherwise noted.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used in this specification, the singular forms "a," "an" and "the" specifically also encompass the plural forms of the terms to which they refer, unless the content clearly dictates otherwise.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, unless specifically indicated otherwise, the word "or" is used in the "inclusive" sense of "and/or" and not the "exclusive" sense of "either/or."

Reference is made hereinafter in detail to specific embodiments of the invention. While the invention will be described in conjunction with these specific embodiments, it will be understood that it is not intended to limit the invention to such specific embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail, in order not to unnecessarily obscure the present invention.

An aspect of the invention provides a method for preparing a dry powder inhalation composition comprising the steps of mixing a first portion of a first particulate inhalant medicament with the carrier to form an first mixture; thereafter mixing the first mixture with a second particulate inhalant medicament to form a second mixture; and mixing the second mixture with a second portion of the first particulate inhalant medicament to form a dry powder inhalation composition. In this aspect, the ratio by weight of the second particulate inhalant medicament to the carrier is less than the ratio by weight of the first particulate inhalant medicament to the carrier.

In one embodiment of this aspect, the first portion of the first medicament is less than half of the total quantity of the first medicament, while in yet other embodiments the first portion of the first medicament is less than 2% weight by weight of the total amount of carrier.

While not wishing to be bound by theory, it is believed that a key aspect of the invention contributing to the uniformity of disposition, reliability and dose uniformity is that the first portion of the first medicament when mixed with the carrier creates a monolayer on the carrier. In an embodiment the first portion of the first medicament comprises a sufficient amount to create a monolayer of the first medicament on the particulate carrier.

The amount of medicament to form a close packed monolayer of first medicament on the carrier can be calculated using the following equation:

$$C^{min} = 2\pi d \frac{(D+d)^2}{\sqrt{3D^3}}$$

where D and d are the volume median diameters (VMD) of the carrier and first medicament respectively. Thus for a carrier with a VMD of approximately 57.5 microns and a first medicament with a VMD of approximately 1.44 microns, $C^{min} \approx 0.1\%$ (w/w). Thus, for example, in blending 2.15 grams of a first medicament with 47.72 grams of a particulate carrier, the first portion of first medicament to be added would be about 0.04772 grams. In some embodiments, the first portion of first medicament is added using a geometric mixing process.

Representative non-limiting examples of particulate carriers for use in the invention include, without limitation, lactose, glucose, or sodium starch glycolate particulates. In some embodiments, the particulate carrier is lactose. The particulate lactose is in some instances alpha lactose monohydrate. In general, the particle size of the lactose should be such that it can be entrained in an air stream but not deposited in the key target sites of the lung. Accordingly, in some embodiments, lactose with a mean particle size of less than 40 μm is excluded. Particle size is determined using laser light scattering (Sympatec GmbH, Claasthal-Zellerfeld, Germany). The carrier particles have a VMD of from about 50 to about 250 μm. Within that range, the carrier particles of a given composition according to the invention may have a VMD of from about 50 to about 60 μm or from about 60 to about 90 μm or from about 90 to about 150 μm.

As used herein, the recitation of a numerical range for a variable is intended to convey that the invention may be practiced with the variable equal to any of the values within that range. Thus, for a variable that is inherently discrete, the variable can be equal to any integer value of the numerical range, including the end-points of the range. Similarly, for a variable that is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

In the exemplified methods and compositions the first medicament is a steroid and the second medicament is a bronchodilator. One of skill in the art will appreciate that the discovery that mixing a carrier with two or more medicaments in the sequential fashion as detailed herein confers certain appealing properties to the resultant composition need not be limited to the exemplified active substances. Hence, in some embodiments, the first medicament is an anti-inflammatory. A steroid contemplated is budesonide. In some embodiments the second medicament is a bronchodilator, in particular a long acting bronchodilator, such as formoterol or a pharmaceutically acceptable salt thereof.

The proportion of first medicament to second medicament by mass will depend on the relative potencies of the medicaments concerned and will generally be known by the skilled person in the art. However, in some embodiments, these proportions may range from about 5:1 to about 100:1. In other embodiments, the proportion of second medicament to carrier will be in the range of from about 10:1 to about 1:10,000.

An aspect of the invention provides a dry powder inhalation composition prepared by a process (as described above) comprising the steps of mixing a carrier with a first portion of a first particulate inhalant medicament to form an first mixture; thereafter mixing the first mixture with a second particulate inhalant medicament to form a second mixture; and mixing the second mixture with a second portion of the first particulate inhalant medicament to form a dry powder inhalation composition. In this aspect, the ratio by weight of the second particulate inhalant medicament to the carrier is less than the ratio by weight of the first particulate inhalant medicament to the carrier.

In some embodiments of this aspect, the first medicament is budesonide while in other embodiments the second medicament is formoterol. In yet other embodiments, the second medicament is formoterol fumarate dihydrate.

The compositions according to the invention are optionally formulated in a pharmaceutically acceptable vehicle with any of the well-known pharmaceutically acceptable medically inert moiety such as carriers, including diluents, excipients, surfactants, and flavourings (see *Remington's Pharmaceutical Sciences*, 18th Ed., Gennaro, Mack Publishing Co., Easton, Pa. 1990 and *Remington: The Science and Practice of Pharmacy*, Lippincott, Williams & Wilkins, 1995). While the type of pharmaceutically acceptable carrier/vehicle employed in generating the compositions of the invention will vary depending upon the mode of administration of the composition to a mammal, generally pharmaceutically acceptable carriers are physiologically inert and non-toxic.

As used herein, "medicament" or "active ingredient" is meant to encompass active pharmaceuticals appropriate for inhalation therapy in dry powder form. Representative, non-limiting examples include bronchodilators (e.g., epinephrine, metaproterenol, terbutaline, albuterol, and the like), anticholinergic agents (e.g., ipratropium bromide), xanthines (e.g., dyphylline, aminophylline), inhalant corticosteroids (e.g., flunisolide, beclomethasone, budesonide, and the like), or .beta.-2 adrenergic receptor agonists (e.g., salmeterol and formoterol).

The medicament may be in any isomeric form or mixture of isomeric forms, for example a pure enantiomer, particularly the R,R-enantiomer, a mixture of enantiomers, a racemate or a mixture thereof (e.g., formoterol). Pharmaceutically acceptable derivatives include pharmaceutically acceptable salts, in particular acid addition salts with inorganic acids such as hydrochloric acid, hydrobromic acid, sulphuric or phosphoric acid. The salt may also be with an organic acid such as acetic, succinic, maleic, furmaric, citric, tartaric, lactic or benzoic. The active ingredient and pharmaceutically acceptable derivatives thereof may exist in the form of a solvate, in particular a hydrate.

A form of active ingredient for use in the invention is formoterol fumarate, especially formoterol fumarate dihydrate, conveniently in its racemic form. Formoterol, salts and hydrates thereof and salt hydrates thereof as described above may be prepared by known methods, for example as described in U.S. Pat. No. 3,994,974 or U.S. Pat. No. 5,684,199.

The formulations of the compositions of the invention may conveniently be presented in unit dosage form and may be prepared by conventional pharmaceutical techniques. Such techniques include the step of bringing into association the compound of the invention and the pharmaceutically acceptable carrier(s), or an excipient. In general, the formulations are prepared by uniformly and intimately bringing into association the active ingredient with finely divided solid carriers, and then, if necessary, preparing discrete dosage units of the product.

The dry powder composition may be metered and filled into capsules, e.g., gelatin or hydroxypropyl methylcellulose capsules, such that the capsule contains a unit dose of active ingredient.

When the dry powder is in a capsule containing a unit dose of active ingredient, the total amount of composition will depend on the size of the capsules and the characteristics of the inhalation device with which the capsules are being used. However, representative characteristic total fill weights of dry powder per capsule are between 1 and 25 mg, e.g., 5, 10, 15 or 20 mg.

Alternatively, the dry powder composition according to the invention may be filled into the reservoir of a multidose dry powder inhaler (MDPI), for example of the kind illustrated in WO 92/10229.

Another aspect of the invention provides for a dry powder inhaler comprising the inhaler and a composition according to the invention.

Another aspect of the invention provides a method for the administration of a particulate medicament, comprising inhalation of a composition of the invention from a multidose dry powder inhaler.

In yet another aspect, the invention provides a method for the administration of a therapeutically effective amount of compositions prepared by the processes described herein, for the treatment of conditions responsive to the medicaments of choice. Non-limiting examples of conditions include chronic obstructive pulmonary disease, asthma, late phase allergic responses, or pulmonary inflammations.

The term "therapeutically effective amount" is used to denote treatments at dosages effective to achieve the therapeutic result sought. Furthermore, one of skill will appreciate that the therapeutically effective amount of the compositions of the invention may be lowered or increased by fine tuning and/or by administering more than one composition of the invention, or by administering a composition of the invention with another compound or composition. The invention therefore provides a method to tailor the administration/treatment to the particular exigencies specific to a given mammal.

The following examples are intended to further illustrate certain preferred embodiments of the invention and are not limiting in nature. Those skilled in the art will recognize, or be able to ascertain, using no more than routine experimentation, numerous equivalents to the specific substances and procedures described herein.

EXAMPLES

Example 1

Preparation of Budesonide/Formoterol/Lactose Blends 100:6 and 200:6 Microgram Budesonide/Formoterol Blends at 2.5 Kilo Scale

| Blend Strength | Lactose | Budesonide | Formoterol |
| --- | --- | --- | --- |
| 100:6 | 2354.25 grams | 137.5 grams | 8.25 grams |
| 200:6 | 2373.8 grams | 122.5 grams | 3.7 grams |

Stage 1

A monolayer of budesonide was formed on the lactose crystals employing 0.5% weight by weight of budesonide. The required amount of lactose and budesonide (see Table I) were dispensed into separate stainless steel containers. Half the lactose was placed into a stainless steel mixing container with a lid. A 4 liter container was used for 1 kilo/2 kilo batches and both 8 liter and 10 liters containers for 2.5 kilo/batches. Any aggregates of budesonide were broken up with a spatula and the active ingredient was gradually added with even distribution over the lactose bed. The remaining lactose was added into the mixing vessel. The mixing vessel was then placed on a TURBULA™ mixer (TURBULA™, Glen Creston, N.J., USA) for 10 minutes at 23 or 32 rpm.

Stage 2

The formoterol was added to the pre-blend from stage 1. The required amount of formoterol (see Table I) was weighed into a stainless steel beaker. The formoterol was added into the mixing container after breaking up any agglomerates with a spatula. This was added a spatula full at a time ensuring even distribution over the blend. The container was then replaced on the TURBULA™ mixer for 40 minutes at 46 rpm.

Stage 3

The rest of the budesonide was added to the blend. The budesonide was dispensed into a stainless steel beaker. Half the pre-blend from stage 2 was added into the 3-liter bowl of an aeromatic fielder pma 1 granulator, (Nivo Pharma Systems (Nivo Inc.) Columbia, Md., US). The budesonide was subsequently added in, carefully ensuring an even distribution around the bowl. The remaining pre-blend was added in. The powder was mixed for 15 minutes with a granulator speed of 1500 rpm and a chopper speed of 600 rpm. The blend was discharged from the mixer into a double polythene bag. The blend was poured into a 250 micron sieve assembly and sieved at amplitude 0.65 millimeters using the Retsch sieve shaker.

Ten samples from different spots of the blend were taken for homogeneity analysis for both budesonide and formoterol. All blends were found to contain drugs close to the targets with relative standard deviation (RSD) of drug content <5% (Table 2).

TABLE 2

Homogeneity Results for Budesonide and Formoterol Blends.

| Batch Number | Budesonide Concentration % w/w | | | Formoterol Concentration % w/w | | |
|---|---|---|---|---|---|---|
| | Target | Actual | % RSD | Target | Actual | % RSD |
| RD-01-020 | 4.90 | 4.9 | 1.8 | 0.148 | 0.152 | 2.9 |
| RD-01-021 | 5.5 | 5.3 | 2.2 | 0.330 | 0.335 | 4.1 |
| RD-01-022 | 4.90 | 4.8 | 1.3 | 0.148 | 0.151 | 2.2 |
| RD-01-023 | 5.5 | 5.3 | 2.0 | 0.330 | 0.336 | 3.2 |

After the blend was found to be homogeneous in drug contents, it was then filled into a IVAX™ multidose DPI (MDPI), a DPI devise based on that disclosed in WO92/10229.

The inhalers that contained the formulation were then tested for pharmaceutical performance under conditions specified in European Pharmacopoeia (2001) including uniformity of delivered dose and fine particle dose. The drug per actuation (DPA) was measured using a dose unit sampling unit in conjunction with a critical flow controller model TPK, high capacity pump and flowmeter (Copley Scientific, Nottingham, U.K.) while fine particle dose (FPD) and fine particle fraction (FPF) were measured using a 5-stage liquid impinger MSL also from Copley Scientific.

The compositions gave excellent dose uniformity and reliability with mean DPA close to label claim for both medicaments when used in association with the device of WO 92/10229, with a good proportion of fine particles of both drugs (Tables 3 & 4).

TABLE 3

Pharmaceutical Assessment Results for the blends for the delivery of 100 mcg Budesonide (Bud) and 6 mcg Formoterol (EML)

| | Device 1 | | Device 2 | | Device 3 | |
|---|---|---|---|---|---|---|
| Batch No. | BUD | EML | BUD | EML | BUD | EML |
| % FPF | | | | | | |
| RD-01-021 | 49.5 | 34.5 | 49.5 | 35.0 | 49.0 | 36.0 |
| RD-01-023 | 50.5 | 38.5 | 52.5 | 39.0 | 51.0 | 37.5 |

TABLE 3-continued

Pharmaceutical Assessment Results for the blends for the delivery of 100 mcg Budesonide (Bud) and 6 mcg Formoterol (EML)

| | Device 1 | | Device 2 | | Device 3 | |
|---|---|---|---|---|---|---|
| Batch No. | BUD | EML | BUD | EML | BUD | EML |
| FPD μg | | | | | | |
| RD-01-021 | 54.9 | 2.4 | 52.3 | 2.3 | 52.4 | 2.4 |
| RD-01-023 | 54.6 | 2.5 | 55.8 | 2.5 | 55.7 | 2.5 |
| Mean DPA | | | | | | |
| RD-01-021 | 111.8 | 6.5 | 105.6 | 6.6 | 108.9 | 6.7 |
| RD-01-023 | 105.8 | 6.3 | 108.6 | 6.5 | 110.6 | 6.6 |

TABLE 4

Pharmaceutical Assessment Results for the blends for the delivery of 200 mcg Budesonide (Bud) and 6 mcg Formoterol (EML)

| | Device 1 | | Device 2 | | Device 3 | |
|---|---|---|---|---|---|---|
| Batch No. | BUD | EML | BUD | EML | BUD | EML |
| % FPF | | | | | | |
| RD-01-020 | 51.5 | 38.0 | 52.0 | 38.0 | 48.0 | 33.5 |
| RD-01-022 | 49.0 | 35.5 | 52.5 | 37.5 | 47.0 | 34.0 |
| FPD μg | | | | | | |
| RD-01-020 | 111.2 | 2.4 | 113.5 | 2.5 | 99.7 | 2.1 |
| RD-01-022 | 97.0 | 2.2 | 103.0 | 2.2 | 95.9 | 2.1 |
| Mean DPA | | | | | | |
| RD-01-020 | 212.0 | 6.3 | 225.6 | 6.7 | 216.3 | 6.5 |
| RD-01-022 | 217.2 | 6.5 | 206.2 | 6.1 | 206.7 | 6.2 |

EQUIVALENTS

While the claimed invention has been described in detail and with reference to specific embodiments thereof, it will be apparent to one of ordinary skill in the art that various changes and modifications can be made to the claimed invention without departing from the spirit and scope thereof. Thus, for example, those skilled in the art will recognize, or be able to ascertain, using no more than routine experimentation, numerous equivalents to the specific substances and procedures described herein. Such equivalents are considered to be within the scope of this invention, and are covered by the following claims.

The invention claimed is:

1. A dry powder inhalation composition prepared by a process comprising the steps of:
   (a) mixing an inert particulate carrier with a first portion of a first particulate inhalant medicament comprising an anti-inflammatory steroid to form a first mixture, wherein said particulate carrier has a volume median diameter (VMD) of from about 50 to about 250 μm, wherein the first portion of the first particulate inhalant medicament is sufficient to create a monolayer of the first particulate inhalant medicament on the particulate carrier;
   (b) mixing said first mixture with a second particulate inhalant medicament comprising a bronchodilator to form a second mixture; and
   (c) mixing said second mixture with a second portion of the first particulate inhalant medicament to form a dry powder inhalation composition, wherein, in the dry powder inhalation composition from step (c), the ratio by weight of the second particulate inhalant medicament to the carrier is less than the ratio by weight of the first particulate inhalant medicament to the carrier, and wherein the dry powder inhalation composition consists of said particulate carrier, said first particulate inhalant medicament and said second particulate inhalant medicament.

2. A dry powder inhalation composition according to claim 1, wherein said anti-inflammatory steroid is budesonide.

3. A dry powder inhalation composition according to claim 1, wherein said bronchodilator is formoterol.

4. A dry powder inhalation composition according to claim 3, wherein said formoterol is formoterol fumarate dihydrate.

5. A dry powder inhalation composition according to claim 1, wherein said particulate carrier has a VMD of from about 50 to about 60 μm.

6. A dry powder inhalation composition according to claim 1, wherein said particulate carrier has a VMD of from about 60 to about 90 μm.

7. A dry powder inhalation composition according to claim 1, wherein said particulate carrier has a VMD of from about 90 to about 150 μm.

8. A multidose dry powder inhaler comprising a composition according to claim 1.

9. A multidose dry powder inhaler comprising a composition according to claim 4.

10. A method for administering a particulate medicament, comprising a step of inhaling from a multidose dry powder inhaler a composition according to claim 1.

11. A method for administering a particulate medicament, comprising a step of inhaling from a multidose dry powder inhaler a composition according to claim 4.

12. A method of preparing a dry powder inhalation composition comprising the steps of:
(a) mixing an inert particulate carrier with a first portion of a first particulate inhalant medicament to form a first mixture, wherein said particulate carrier has a volume median diameter (VMD) of from about 50 to about 250 μm, wherein the first portion of the first particulate inhalant medicament is sufficient to create a monolayer of the first particulate inhalant medicament on the particulate carrier;
(b) mixing said first mixture with a second particulate inhalant medicament to form a second mixture; and
(c) mixing said second mixture with a second portion of the first particulate inhalant medicament to form a dry powder inhalation composition,
wherein, in the dry powder inhalation composition from step (c), the ratio by weight of the second particulate inhalant medicament to the carrier is less than the ratio by weight of the first particulate inhalant medicament to the carrier.

13. A method according to claim 12, wherein the first portion of the first particulate inhalant medicament is less than half weight by weight of the total amount of the first particulate inhalant medicament in the dry powder inhalation composition.

14. A method according to claim 12, wherein the first portion of first particulate inhalant medicament is less than 2% weight by weight of the total amount of the particulate carrier.

15. A method according to claim 12, wherein the particulate carrier is lactose.

16. A method according to claim 12, wherein the ratio of the first particulate inhalant medicament to the second particulate inhalant medicament by weight is from 5:1 to 100:1.

17. The method of claim 12, wherein the dry powder inhalation composition of step (c) consists of said particulate carrier, said first particulate inhalant medicament and said second particulate inhalant medicament.

18. A method of preparing a dry powder inhalation composition comprising the steps of:
(a) mixing an inert particulate carrier with a first portion of a first particulate inhalant medicament comprising an anti-inflammatory steroid to form a first mixture, wherein said particulate carrier has a volume median diameter (VMD) of from about 50 to about 250 μm, wherein the first portion of the first particulate inhalant medicament is sufficient to create a monolayer of the first particulate inhalant medicament on the particulate carrier;
(b) mixing said first mixture with a second particulate inhalant medicament comprising a bronchodilator to form a second mixture; and
(c) mixing said second mixture with a second portion of the first particulate inhalant medicament to form a dry powder inhalation composition,
wherein, in the dry powder inhalation composition from step (c), the ratio by weight of the second particulate inhalant medicament to the carrier is less than the ratio by weight of the first particulate inhalant medicament to the carrier.

19. A method according to claim 18, wherein the first portion of the first particulate inhalant medicament is less than half weight by weight of the total amount of the first particulate inhalant medicament in the dry powder inhalation composition.

20. A method according to claim 18, wherein said particulate carrier comprises lactose.

21. A method according to claim 18, wherein said anti-inflammatory steroid is budesonide.

22. A method according to claim 18, wherein said bronchodilator is formoterol.

23. A method according to claim 18, wherein the ratio of said first particulate inhalant medicament to said second particulate inhalant medicament by weight is from 5:1 to 100:1.

* * * * *